United States Patent [19]

Chen et al.

[11] Patent Number: 5,741,316

[45] Date of Patent: Apr. 21, 1998

[54] ELECTROMAGNETIC COIL CONFIGURATIONS FOR POWER TRANSMISSION THROUGH TISSUE

[75] Inventors: James C. Chen, Bellevue; Brian D. Wilkerson, Redmond; Darrin Huston; David J. Brown, both of Enumclaw, all of Wash.

[73] Assignee: Light Sciences Limited Partnership, Issaquah, Wash.

[21] Appl. No.: 756,945

[22] Filed: Dec. 2, 1996

[51] Int. Cl.$^6$ .............................. A61N 1/378; A61N 1/36; A61N 1/00

[52] U.S. Cl. ................................. 607/61; 607/65

[58] Field of Search .................. 607/61, 2, 65, 607/33, 55–57

[56] References Cited

U.S. PATENT DOCUMENTS

| | | | |
|---|---|---|---|
| 4,143,661 | 3/1979 | LaForge et al. | 607/61 |
| 4,421,115 | 12/1983 | Kraus | 607/61 |
| 4,736,747 | 4/1988 | Drake | 607/61 |
| 5,000,178 | 3/1991 | Griffith | 607/2 |
| 5,030,236 | 7/1991 | Dean | 623/16 |
| 5,095,905 | 3/1992 | Klepinski | 607/118 |
| 5,193,539 | 3/1993 | Schulman et al. | 607/61 |
| 5,314,453 | 5/1994 | Jeutter | 607/61 |
| 5,350,413 | 9/1994 | Miller | 607/61 |
| 5,411,537 | 5/1995 | Munshi et al. | 607/33 |
| 5,540,735 | 7/1996 | Wingrove | 607/46 |

FOREIGN PATENT DOCUMENTS

| | | | |
|---|---|---|---|
| 602195 | 4/1978 | U.S.S.R. | 607/33 |

OTHER PUBLICATIONS

H. Matsuki et al., "Implantable transformer for an artificial heart utilizing amorphous magnetic fibers," *J. Appl. Phys.*, 64(10), 15 Nov. 1988, ©1988 American Institute of Physics, pp. 5859–5861.

E. Tatsumi et al., "Development of an Electrohydraulic Total Artificial Heart System," pp. 101–107.

J. Miller et al., "Development of an Automated Transcutaneous Energy Transfer System," *ASAIO Journal 1993*, Slide Forum–Prosthetics 5, From the Cardiovascular Devices Division, University of Ottawa Heart Institute, Ottawa, Ontario, Canada, pp. M706–M710.

D. Selby et al., "Inductive Coupling for Recharging Nickel Cadmium Batteries in Implanted Cardiac Pacemakers," vol., X Trans. Amer. Soc. Artif. Int. Organs, 1964, pp. 371–372.

(List continued on next page.)

*Primary Examiner*—William E. Kamm
*Assistant Examiner*—Carl H. Layno
*Attorney, Agent, or Firm*—Ronald M. Anderson

[57] ABSTRACT

Several embodiments of relatively compact transmitter coils and receiver coils having an improved transcutaneous power transfer efficiency. The transmitter coils are preferably applied to the outer surface of a cutaneous layer on a patient's body and held in place using adhesive tape or other appropriate supporting material. Implanted within the patient's body is a receiver coil. To improve the power transfer efficiency of one embodiment, a transmitter coil and receiver coil include cores having pole faces with a substantially larger area than the cross section of the core at other locations. In addition, the core of the receiver coil is substantially shorter than that of the transmitter coil so that the lines of flux produced by the transmitter coil tend to pass through the pole faces of the receiver coil in greater density than they would if the pole faces of the transmitter and receiver cores were spaced identically. Relatively compact configurations for the transmitter core include an angled portion adjacent each of the pole faces so that the main portion of the transmitter core is disposed generally parallel and closely spaced to the surface of the cutaneous layer against which the transmitter core is placed. Further, two separate transmitter windings are provided on the transmitter core with an intermediate section joining the portions of the core on which these windings are disposed. This configuration provides enhanced power transfer capability compared to using a single winding around the intermediate section of the core.

34 Claims, 4 Drawing Sheets

OTHER PUBLICATIONS

H. Matsuki et al., "Simulations of Temperature Rise on Transcutaneous Energy Transmission by Non–contact Energy Transmitting Coils," IEEE Transactions on Magnetics, vol. 29, No. 6, Nov. 1993, ©1993, ©1993 IEEE, pp. 3334 and 3336.

G. Loeb et al., "Injectable microstimulator for functional electrical stimulation," MBEC, North Sea special feature, Med., & Biol. Eng. & Comput., 1991, 29, Nov. 1991, pp. NS13–NS19.

C. Andren et al., "The Skin Tunnel Transformer: A New System that Permits Both High Efficiency Transfer of Power and Telemetry of Data Through the Intact Skin," IEEE Transactions on Bio–Medical Engineering, vol. BME–15, No. 4, Oct. 1968, pp. 278–280.

H. Matsuki et al., "A New Cloth Inductor Using Amorphous Fiber," IEEE Transactions on Magnetics, vol.MAG–21, No. 5, Sep. 1985, pp. 1738–1740.

D. Melvin et al., "Electric Power Induction Through an Isolated Intestinal Pouch," vol. XXXVII Trans Am Soc Artif Intern Organs 1991, Slide Forum 8, Circulatory Assist–VAD Control and Energy Systems, pp. M203–M204.

G. Myers et al., "A Transcutaneous Power Transformer," Supported by NIH Contract #PH–43067–1414, 5 pages.

T. Mussivand et al., "Transcutaneous Energy Transfer System Performance Evaluation," *Artificial Organs*, 17(11):940–947, Blackwell Scientific Publications, Inc., Boston, ©1993 International Society for Artificial Organs.

J. Mackenzie et al., "Radio–Frequency Energy Transport into the Body," Journal of Surgical Research, vol. 7, No. 3, Mar. 1967, pp. 133–144.

M. Soma et al., "Radio–Frequency Coils in Implantable Devices: Misalignment Analysis and Design Procedure," IEEE Transactions on Biomedical Engineering, vol. BME–34, No. 4, Apr. 1987, pp. 276–282.

Y. Mitamura et al., "Transcutaneous Energy Transmission for Assisted Circulation," Assisted Circulation 3, Chapter 48, F. Unger (Ed.), ©Springer–Verlag Berlin Heidelberg 1989, pp. 569–579.

C. Ren et al., "A Novel Electric Design for Electromagnetic Stimulation—The Slinky Coil," IEEE Transactions on Biomedical Engineering, vol. 42, No. 9, Sep. 1995, pp. 918–925.

J. Schuder et al., "The Silicon Diode as a Receiver for Electrical Stimulation of Body Organs," vol. X Trans. Amer. Soc. Artif. Int. Organs, 1964, pp. 366–369.

Kenneth J. Dormer et al., "The Use of Rare–Earth Magnet Couplers in Cochlear Implants," The Laryngoscope 91:Nov. 1981, pp. 1812–1820.

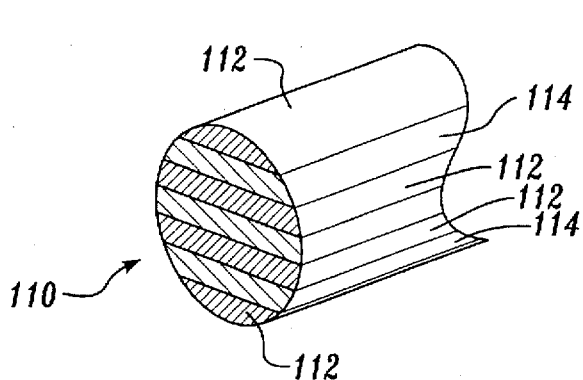
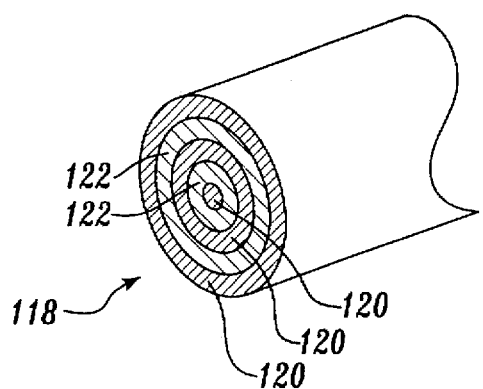
Fig. 8  Fig. 9
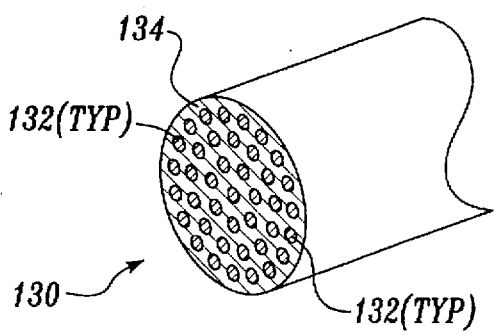
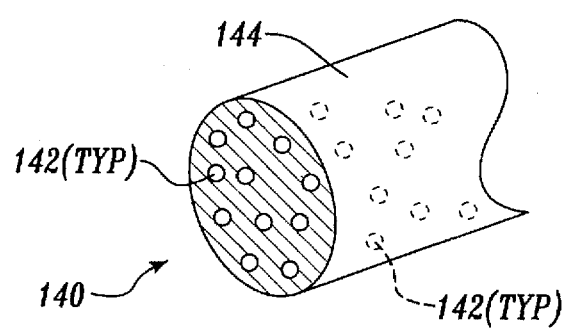
Fig. 10  Fig. 11
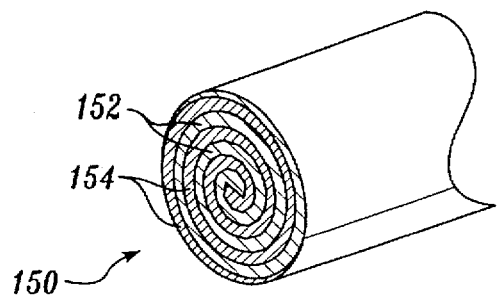
Fig. 12

ELECTROMAGNETIC COIL CONFIGURATIONS FOR POWER TRANSMISSION THROUGH TISSUE

FIELD OF THE INVENTION

The present invention is generally directed to devices for electromagnetically conveying power across an interface, and more specifically, to transmitter and receiver coils that are used to convey power transcutaneously to a medical device implanted within a body of a patient.

BACKGROUND OF THE INVENTION

The use of implanted medical devices such as pacemakers, artificial hearts, and nerve stimulators has become increasingly more prevalent with the continuing development of medical technology. These types of devices are usually energized with an electrical current supplied from a rechargeable implanted battery or from an external source. While it is possible to directly connect an external power supply to an implanted medical device via leads that extend transcutaneously from the patient's body, the risk of infection and other complications makes it preferable to couple power to the implanted devices without passing leads through the skin. One approach that is used provides for supplying power to the implanted device through a radio frequency (RF) energy transfer from an external transmitter. The RF signal produced by the transmitter is transmitted through the skin to an RF receiver that is connected to a power supply on the implanted device. Typically, the received RF signal must be converted to a direct current (DC) signal that is employed to power the implanted device. However, the energy transfer efficiency of such systems is relatively poor across larger gaps.

An alternative approach for transcutaneous power transmission employs an electromagnetic transmitter coil that is energized with a relatively low frequency (e.g., 60 Hz) alternating current (AC) signal, producing a magnetic field that induces a corresponding current in an implanted electromagnetic receiver coil. For example, "C-shaped" half toroidal core transmitter and receiver coils usable to transmit power transcutaneously are disclosed in commonly assigned U.S. patent application Ser. No. 08/451,831 (allowed) and set to issue as U.S. Pat. No. 5,571,152 and U.S. patent application Ser. No. 08/705,334, filed Aug. 29, 1996. While the configuration of a C-shaped core having a plurality of turns of conductor wound about its central portion that is shown in these applications provides for relatively good power transfer, it would clearly be preferable to develop transmitter and receiver coils that are more efficient and comparatively more compact than those disclosed in these earlier references.

The C-shaped core used for the coils in these prior application has two problems. First, the transmitter core tends to extend outwardly too far from the skin's surface, making it more difficult to attach and mount the transmitter coil in a proper disposition, for example, at a site on the chest of a patient. The mass and profile of the C-shaped core cause it to extend outwardly from the surface of the skin. It is contemplated that the core might be secured in place with adhesive tape of other suitable binding material during the transfer of power to the internal receiving coil. However, the C-shaped coil extends outwardly sufficiently far that it would likely be difficult to maintain the pole faces of the core against the skin surface as required for efficient transcutaneous power transfer. In addition, the receiving coil should also be relatively compact, and should have a low profile to minimize the internal volume required to position it adjacent the dermal layer in the patient's body. Secondly, it is important that the transmitter and receiver coils tolerate at least some misalignment between their pole faces, since it may not be possible to determine the exact position of an implanted receiving coil when mounting the transmitter coil to the skin of the patient. In addition, it is desirable that the configuration and size of the core of the transmitting coil and of the receiving coil be optimized for the transcutaneous power transfer to occur over the required distances. Most conventional transformers are designed to couple over relatively short gaps between their respective pole faces, but the gap between the pole faces of the transmitter coil core and the receiver coil core used for transcutaneous power transmission may be several centimeters.

SUMMARY OF THE INVENTION

In accord with the present invention, an electromagnetic coil configuration for conveying power transcutaneously is defined that includes a core of magnetically permeable material having a first pole face coupled to a second pole face by an intermediate section. The intermediate section has a smaller cross-sectional size than that of the first and second pole faces to provide an increased pole face area for conveying a transcutaneous magnetic flux. A plurality of turns of an electrical conductor are wound around the intermediate section. This electrical conductor carries an induced current if the coil is used as a receiver that is electromagnetically excited by an external source of the transcutaneous magnetic flux. Alternatively, if the coil is used as a transmitter of the transcutaneous magnetic flux, the turns of the electrical conductor carry a varying electrical current supplied by a power supply to which the electrical conductor is adapted to be connected.

In one embodiment, the intermediate section comprises a first section and a second section that are respectively coupled to the first pole face and the second pole face. The first section has a first winding comprising a portion of the plurality of the turns of the electrical conductor, and the second section has a second winding comprising another portion of the plurality of the turns of the electrical conductor. In one configuration, the first section is directly coupled to the second section, and the core is generally V-shaped. In another configuration, the intermediate section further comprises a third section that extends between the first section and the second section, so that the core is generally U-shaped. Preferably, the first and second sections include an angled portion disposed adjacent to the first and second pole faces, enabling the first and second sections to extend generally to one side of the first and second pole faces, so that the core has a low profile relative to the first and second pole faces.

In another embodiment, the intermediate section includes a mid-portion that is elongate and flattened, and which extends in a direction generally parallel to the first and second pole faces. The plurality of turns of the electrical conductor are wound around the mid-portion.

It is also preferable that the core comprise a plurality of layers of the magnetically permeable material, adjacent layers of the magnetically permeable material being separated by a layer of a dielectric material, to minimize losses in the core due to eddy currents. The same result is achieved if the core comprises a plurality of discrete elements such as particles or rods that are formed of the magnetically permeable material, which are bonded together with a dielectric material.

Another aspect of the present invention is directed to a system that includes a transmitter coil and a receiver coil for transcutaneously transferring power. A cross-sectional size of the first and second pole faces of the transmitter substantially differs from the cross-sectional size of the first and second pole faces of the receiver. Preferably, the transmitter core is longer than the receiver core and an area of the first and second pole faces of the transmitter core is substantially greater than that of the first and second pole faces of the receiver core.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 8 is a cut-away view of a cross section through a core of a transmitter or receiver coil that includes a plurality of longitudinally extending stacked layers of a magnetically permeable material alternating with a dielectric material;

FIG. 9 is a cut-away view of a cross section through a core of a transmitter or receiver coil that includes a plurality of concentric layers of magnetically permeable material alternating with a dielectric material;

FIG. 10 is a cut-away view of a cross section through a core of a transmitter or receiver coil that includes a plurality of rods of magnetically permeable material bound in a matrix of a dielectric material;

FIG. 11 is a cut-away view of a cross section through a core of a transmitter or receiver coil that includes a plurality of particles of magnetically permeable material bound in a matrix of a dielectric material; and FIG. 12 is a cut-away view of a cross section through a core of a transmitter or receiver coil comprising helically rolled sheets of a magnetically permeable material and a dielectric material.

DESCRIPTION OF THE PREFERRED EMBODIMENTS

Transmission and receiver coils previously developed for transcutaneous power transmission to energize a probe to administer photodynamic therapy (PDT) have included a "C-shaped" core around which was wound a helical coil of an electrical conductor. The transmitter coil in this system is adapted to be coupled to an external power supply that provides a 60 Hz AC. When the electrical current flows through the windings of the transmitter coil, power is transmitted over a distance of several centimeters to a similarly shaped receiver coil that is coupled to a plurality of light emitting diodes (LEDs) in an implantable PDT probe. Ongoing efforts to develop more efficient designs for the transmitter and receiver coils have resulted in the present invention.

Figure 1:
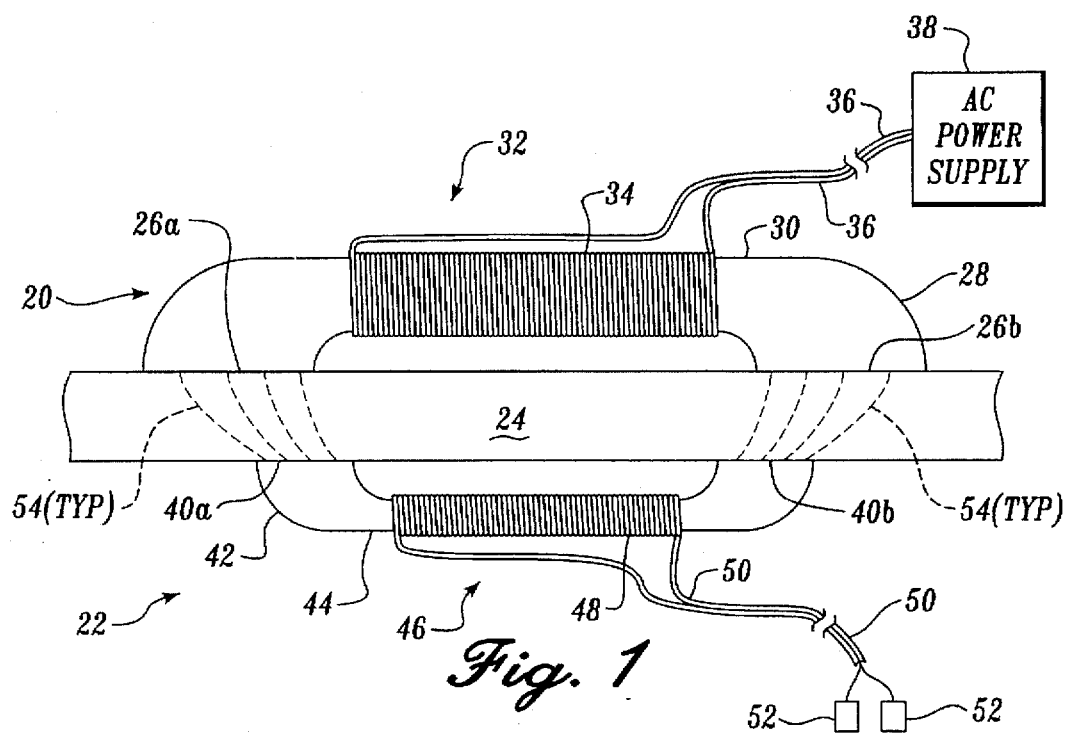
FIG. 1 is a side view of first embodiments of a transmitter coil and a receiver coil for transcutaneously coupling power in accord with the present invention.
Figure 2:
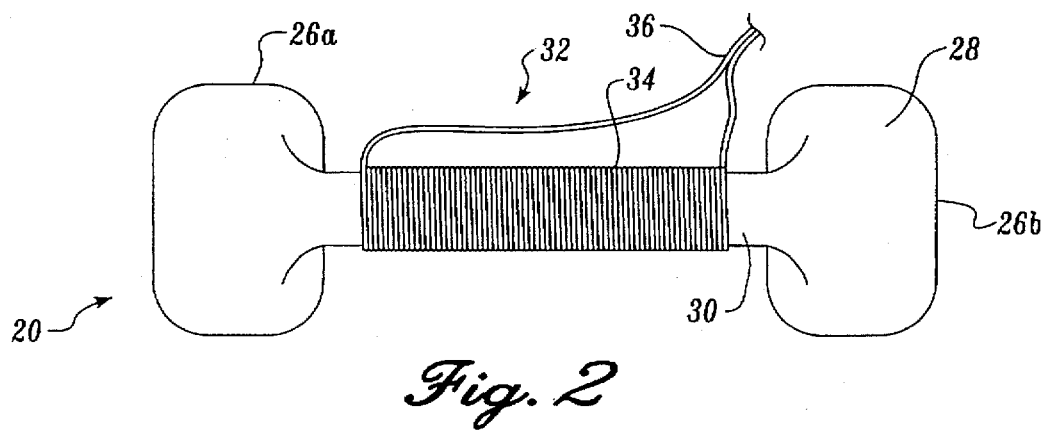
FIG. 2 is a plan view of the first embodiment of the transmitter coil, which is substantially similar in appearance to the receiver coil.

FIG. 1 shows a first embodiment of the present invention in which a transmitter coil 20 is electromagnetically coupled to a receiver coil 22 to convey power transcutaneously through an intervening cutaneous layer 24. In this embodiment of the invention, core faces 26a and 26b of a core 28 have a surface area that is substantially larger than a cross-sectional area of the remaining portion of the core. The larger surface area results from flaring the ends of core 28 outwardly proximate core faces 26a and 26b. FIG. 2 illustrates the relative size of core faces 26a and 26b compared to the remainder of core 28.

Core 28 includes an intermediate section 30 that connects the two portions of the core on which core faces 26a and 26b are disposed. A transmitter winding 32 comprises a plurality of turns of an electrical conductor 34, preferably in two or more layers of helical windings, since the flux density produced by transmitter coil 20 is directly proportional to the number of turns of electrical conductor 34 that are wrapped around intermediate section 30. A lead 36 extends from transmitter winding 32 to an AC power supply 38, that would likely be connected to an AC line. It is also contemplated that AC power supply 38 can include an external battery pack and an inverter (neither shown). Also, the current supplied through lead 36 can have a sinusoidal, pulse, or other time varying waveform. Furthermore, in the preferred embodiment, the frequency of the electrical current supplied to transmitter coil 20 is preferably less than 500 Hz, since the electromagnetic coupling between transmitter coil 20 and receiver coil 22 has been found to be more efficient at the typical spacing between the transmitter and receiver coil at such frequencies. Another advantage of using a relatively low frequency electrical current is that radio frequency shielding around the transmitter coil is not required.

Receiver coil 22 is generally similar to transmitter coil 20, except that it is relatively more compact and shorter in length. Pole faces 40a and 40b on the ends of a core 42 of receiver coil 22 are also relatively larger in area than other portions of the core and are formed by flaring out the ends of core 42 proximate to the pole faces. An intermediate section 44 couples the portions of core 42 on which pole faces 40a and 40b are disposed. Wrapped around intermediate section 44 is a receiver winding 46 comprising a plurality of turns of an electrical conductor 48, preferably in two or more layers. Electrical conductor 48 is connected through a lead 50 to terminals 52 that are adapted for coupling the receiver coil to a medical device (not shown), which is implanted within the body of the patient, so that electrical current induced to flow within receiver winding 46 can be used to energize the medical device.

Further details of cores 28 and 42 are discussed below, in connection with various configurations used to avoid losses due to eddy currents circulating therein. Preferably, cores 28 and 42 are fabricated using a material that has a relatively high magnetic permeability, such as μ metal or other alloys typically used for electromagnetic cores. It has been found that enhanced performance is obtained for coupling power transcutaneously between transmitter coil 20 and receiver coil 22 by making the length of core 42 sufficiently shorter than that of core 28 so that for a given thickness of cutaneous layer 24, lines of electromagnetic flux 54 tend to flow between pole faces 26a and 26b in a direction passing through corresponding pole faces 40a and 40b of the receiver coil. To optimize power transfer between the coils, the spacing between core faces 26a and 26b should be substantially greater than the thickness of cutaneous layer 24. Previously it was thought that the length of core 28 should equal that of core 42, making the distance between the center of the pole faces of the transmitter coil equal to the distance between the center of the pole faces of the transmitter coil. However, it has been determined that by making the distance between the center of the pole faces of the receiver coil shorter than that between the centers of the pole faces of the transmitter coil, the flux density passing through the pole faces of the receiver coil is increased, thereby enhancing the efficiency of the transcutaneous power transfer process.

Figure 3:
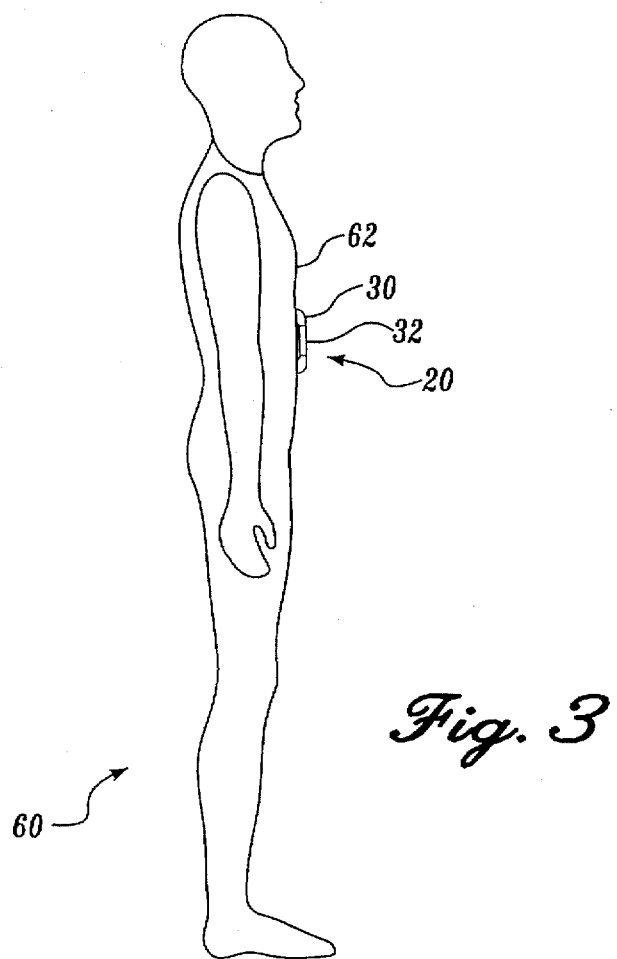
FIG. 3 is a side elevational view of a patient in which a medical device has been implanted, showing the first embodiment of the transmitter coil positioned on the patient's torso to couple power transcutaneously to a receiver coil (not shown) within the patient's body.

Referring now to FIG. 3, a patient 60 is schematically illustrated to show how transmitter coil 20 is applied to a torso 62 of the patient for transcutaneous power transfer to a receiver (not shown), which is implanted immediately opposite transmitter coil 20, inside the patient's body. If transmitter coil 20 is intended to be used while patient 60 is mobile, the external power source (not shown in this Figure) could be attached to a belt worn by the patient and would include a storage battery. Furthermore, transmitter coil 20 can be adhesively secured to torso 62 of the patient to facilitate the transcutaneous power transfer required to energize an internal implanted medical device that is coupled to the receiver coil. Because of the relatively low profile of transmitter coil 20, it can be covered by loose garments so that its use by patient 60 is not evident to others. The patient can then enjoy the freedom of pursuing normal activities while the implanted medical device provides its intended therapeutic benefit.

Figure 4:
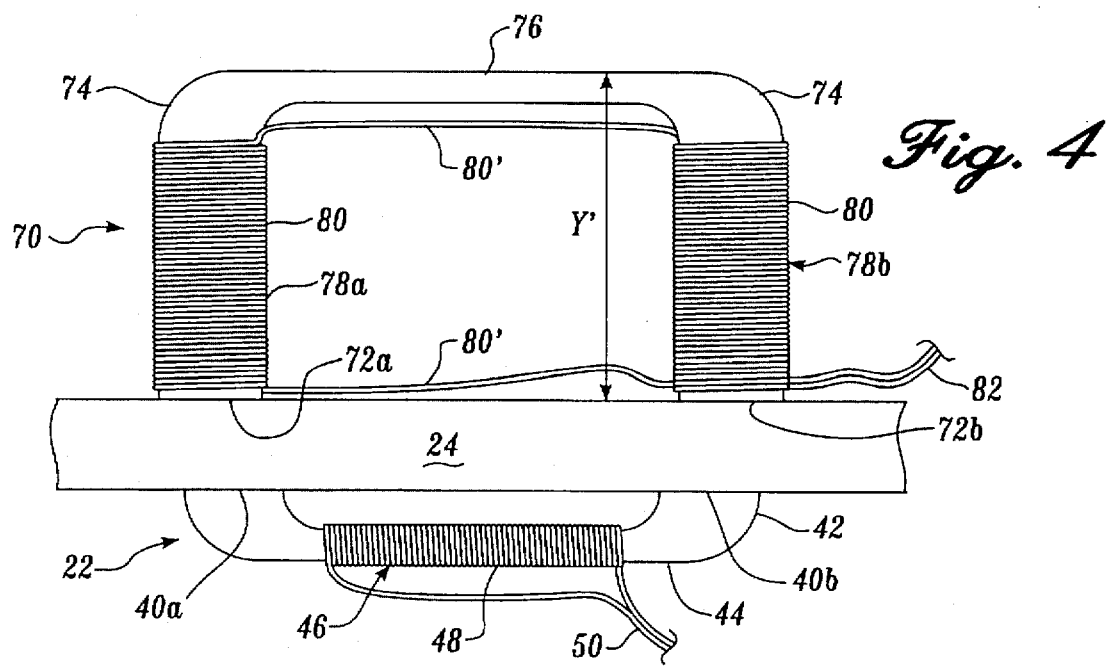
FIG. 4 is a side view of a second embodiment of a transmitter coil and the receiver coil of FIG. 1, disposed on opposite sides of a tissue layer.

FIG. 4 illustrates a second embodiment of a transmitter coil 70. Transmitter coil 70 includes a core 74 having pole faces 72a and 72b disposed at each end. Core 74 extends upright above the respective pole faces and includes an intermediate section 76 that is generally transverse to the upright portions of the core connecting the two sections on which are disposed transmitter windings 78a and 78b. These transmitter windings each comprise a plurality of turns of an electrical conductor 80, preferably in multiple layers. Interconnecting electrical conductors 80' convey electrical current between transmitter windings 78a and 78b, and a lead 82 is provided for connecting the transmitter coil to a power supply (like power supply 38, shown in FIG. 1). Core 74 can be formed as a contiguous assembly with intermediate section 76, or alternatively, the two upright portions and the intermediate section can be fabricated separately and connected together to provide a continuous flux path coupling transmitter windings 78a and 78b so that the magnetic flux produced by the flow of an electrical current through electrical conductor 80 flows through intermediate section 76 of core 74. The transmitter windings 78a and 78b around the two upright portions of core 74 include a plurality of turns of electrical conductor 80 wrapped in a plurality of layers. The two transmitter windings are coupled together by leads 80'. It should be clear that the direction of the transmitter winding turns about each portion of core 74 is such that the magnetic flux they produce reinforces rather than cancels in core 74.

As indicated in FIG. 4, the overall distance between the center of pole faces 72a and 72b is substantially greater than that between the centers of pole faces 40a and 40b of receiver coil 22. This relationship between the relative lengths of the transmitter coil and receiver coil cores, as described above, provides improved efficiency for the transcutaneous power transfer between the two devices. Also, the distance between pole faces 72a and 72b should again be substantially greater than the thickness of cutaneous layer 24.

One of the problems with the design for transmitter coil 70 as shown in FIG. 4 is its relative height Y' above the surface of cutaneous layer 24. As noted above, it is contemplated that the transmitter coil will be attached to the outer surface of cutaneous layer 24 using adhesive tape or other suitable binding material (not shown). Further, it was noted above that it would be desirable to easily hide a transmitter coil under loose clothing. However, due to the relative height of transmitter coil 70 compared to that of the much more compact transmitter coil 20, it will be apparent that securing transmitter coil 70 to patient 60 so that the transmitter coil remains upright with pole faces 72a and 72b in continuous contact with the surface of cutaneous layer 24 would be more difficult, since the transmitter coil would be more likely to shift and lean away from its desired upright position relative to the outer surface of the cutaneous layer against which it is affixed. Moreover, transmitter coil 70, which may have a height (dimension "Y") that is more than two inches, is far too evident and difficult to hide, even under loose clothing, because of the distance that it extends above the cutaneous layer.

Figure 5:
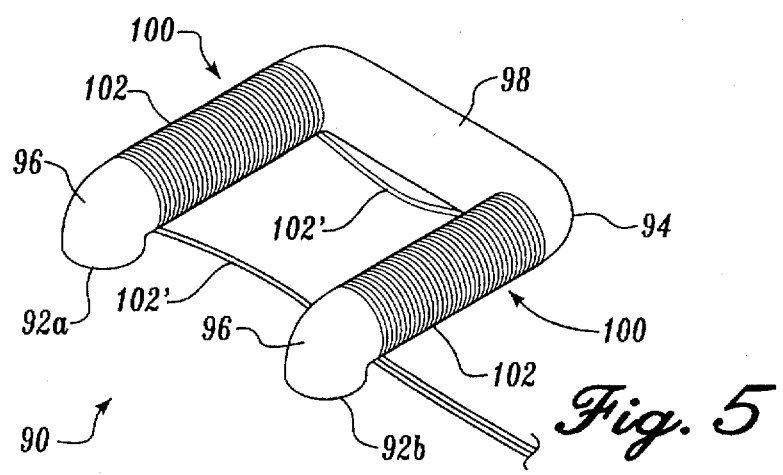
FIG. 5 is an isometric view of a third embodiment of a transmitter or receiver coil.

A solution to this problem is shown in FIG. 5, which illustrates a transmitter coil 90. In this embodiment, pole faces 92a and 92b are disposed at opposite ends of a core 94. However, unlike core 74 of transmitter coil 70, core 94 includes two angled portions 96 adjacent each end; at angled portions 96, the core turns through an angle of approximately 90° so that a plane through the upper portion of the core is generally parallel to pole faces 92a and 92b. Core 94 also includes an intermediate section 98 joining the two portions of the core about which transmitter windings 100 are formed from turns of an electrical conductor 102. As in the previous embodiments, the transmitter windings around each of these portions of core 94 include a plurality of turns of electrical conductor 102 in a plurality of layers. The two transmitter windings are coupled together by leads 102'. Again, the direction of the transmitter winding turns about each portion of core 94 is such that the magnetic flux they produce reinforces rather than cancels in core 94. Since most of core 94 is disposed relatively close to the plane of core faces 92a and 92b, transmitter coil 90 can more readily be affixed to the surface of the cutaneous layer through which electromagnetic power is transferred to a corresponding receiving coil, such as receiving coil 22. In addition, transmitter coil 90 will be less evident under the clothing of a patient, since it does not extend very high above the surface of the cutaneous layer.

Figure 6:
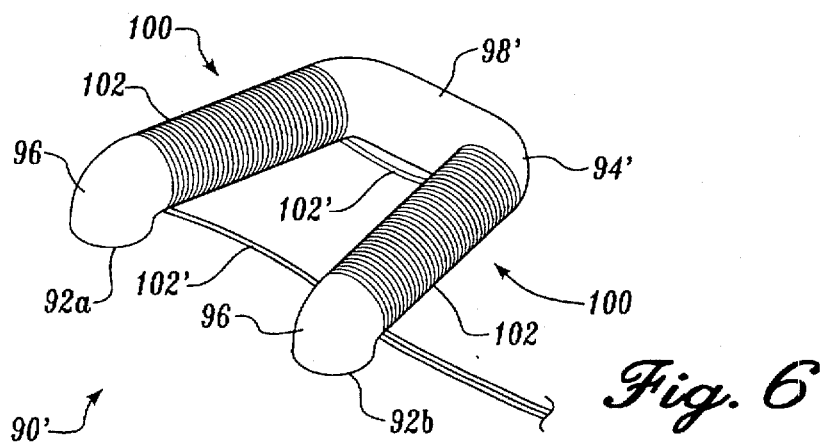
FIG. 6 is an isometric view of a fourth embodiment of a transmitter or receiver coil.
Figure 7:
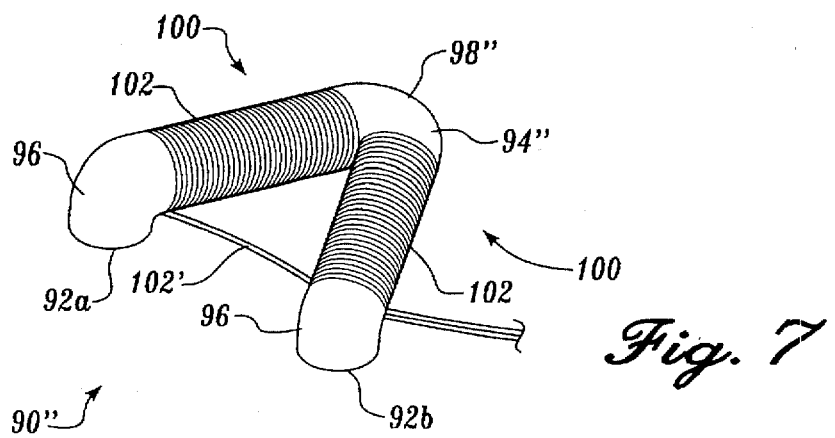
FIG. 7 is an isometric view of a fifth embodiment of a transmitter or receiver coil.

Alternative configurations of the embodiment just discussed above are shown in FIGS. 6 and 7. In FIG. 6, a transmitter coil 90' includes an intermediate section 98', which is relatively shorter than intermediate section 98 of transmitter coil 90. Carrying this modification to its next logical step, a transmitter coil 90" in FIG. 7 is generally V-shaped, so that intermediate section 98" simply joins the two portions of a core 94" on which transmitter windings 100 are disposed.

Turning now to FIGS. 8–12, a plurality of configurations for the core of the transmission coil and/or receiver coil in each of the above-described embodiments are illustrated. In FIG. 8, a core configuration 110 comprises alternating layers 112 of a μ metal or other alloy of the type conventionally used in electromagnetic coils, and layers 114 of a dielectric material. The dielectric material in layers 114 separates the material of layers 112, which has a relatively high magnetic permeability, minimizing eddy currents that cause substantial loss in solid cores of a material that has a high magnetic permeability.

In FIG. 9, a core configuration 118 includes alternating concentric layers 120 and 122. Layers 120 comprise the material having a relatively high magnetic permeability, such as μ metal or other alloy conventionally used in fabricating electromagnetic cores, and layers 122 comprise a dielectric material, such as various types of polymers characterized by having a relatively high dielectric constant.

FIG. 10 shows a core configuration 130 in which a plurality of generally parallel, elongate rods 132 extend through the core in spaced-apart array, bonded in that matrix configuration by a dielectric material 134. As noted above, dielectric material 134 preferably comprises a polymer or other suitable dielectric material. Rods 132 may be formed of μ metal or other alloy conventionally used to fabricate electromagnetic cores.

In FIG. 11, a core configuration 140 comprises a plurality of spaced-apart particles 142 of a material having a relatively high magnetic permeability, such as μ metal, formed as a matrix bound by a material 144 that has a relatively high dielectric property. Once again, a polymer is preferably used for the dielectric material in this configuration.

Finally in FIG. 12, a further alternative core configuration 150 is shown. Core configuration 150 comprises a flexible sheet 152 of a material having a relatively high magnetic permeability, such as μ metal, that is helically rolled with a flexible sheet 154 of a material having a relatively high dielectric property. An appropriate flexible polymer is preferably used for the dielectric material in this embodiment.

Although the present invention has been described in connection with several preferred forms of practicing it, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An electromagnetic coil configuration for conveying power transcutaneously, comprising:
    (a) a core of a magnetically permeable material having a first pole face coupled to a second pole face by an intermediate section, a transverse cross-sectional area of said intermediate section being substantially less than a transverse cross-sectional area of said first and second pole faces to provide an increased pole face area for conveying a transcutaneous magnetic flux; and
    (b) a plurality of turns of an electrical conductor wound around said intermediate section, said electrical conductor carrying an induced current if the coil is used as a receiver that is electromagnetically excited by an external source of the transcutaneous magnetic flux, and carrying a varying electrical current supplied by a power supply to which the electrical conductor is adapted to be connected if the coil is used as a transmitter of the transcutaneous magnetic flux.

2. The electromagnetic coil configuration of claim 1, wherein the intermediate section comprises a first section and a second section that are respectively coupled to the first pole face and the second pole face, said first section having a first winding comprising a portion of the plurality of the turns of the electrical conductor, and said second section having a second winding comprising another portion of the plurality of the turns of the electrical conductor.

3. The electromagnetic coil configuration of claim 2, wherein the first section is connected to the second section, and the core has a general V-shape.

4. The electromagnetic coil configuration of claim 2, wherein the intermediate section further comprises a third section that extends between the first section and the second section, so that the core is generally U-shaped.

5. The electromagnetic coil configuration of claim 2, wherein the first and second sections include an angled portion disposed adjacent to the first and second pole faces, said first and second sections extending generally to one side of the first and second pole faces, so that said core has a low profile relative to the first and second pole faces.

6. The electromagnetic coil configuration of claim 1, wherein the intermediate section includes a mid-portion that extends in a direction generally parallel to the first and second pole faces, said plurality of turns of the electrical conductor being wound around said mid-portion.

7. The electromagnetic coil configuration of claim 1, wherein the core comprises a plurality of layers of the magnetically permeable material, adjacent layers of the magnetically permeable material being separated by a layer of a dielectric material, to minimize losses in the core due to eddy currents.

8. The electromagnetic coil configuration of claim 1, wherein the core comprises a plurality of discrete elements formed of the magnetically permeable material that are bonded with a dielectric material, to minimize losses in the core due to eddy currents.

9. The electromagnetic coil configuration of claim 8, wherein the discrete elements comprise elongate rods that extend through the core.

10. A system for transferring power transcutaneously to energize an implanted medical device within a patient's body, comprising:
    (a) a transmitter coil adapted to be disposed external to the patient's body, said transmitter coil including:
        (i) a transmitter corn of a magnetically permeable material having a first pole face coupled to a second pole face by an intermediate section; and
        (ii) a plurality of turns of an electrical conductor wound around said intermediate section;
    (b) a receiver coil adapted to be disposed subdermally, inside the patient's body, said receiver coil including:
        (i) a receiver core of a substantially solid and magnetically permeable material having a first pole face coupled to a second pole face by an intermediate section, said first and second pole faces having a substantially different transverse cross-sectional area than the first and second pole faces of the transmitter coil; and
        (ii) a plurality of turns of an electrical conductor wound around said intermediate section and having ends adapted to couple to the medical device; and
    (c) a power supply adapted to couple to the turns of the electrical conductor wound around the intermediate section of the transmitter core, said power supply supplying a time varying electrical current to energize the transmitter coil, producing an electromagnetic field that couples transcutaneously with the receiver coil, causing a corresponding electrical current to flow in the receiver coil for energizing the medical device implanted inside the patient's body.

11. The system of claim 10, wherein the first and second pole faces of the receiver coil have a substantially smaller transverse cross-sectional area than that of the first and second pole faces of the transmitter coil.

12. The system of claim 10, wherein the intermediate section of the transmitter coil has a transverse cross-sectional area that is substantially smaller than the transverse cross-sectional area of either of the first and second pole faces of the transmitter coil.

13. The system of claim 10, wherein the intermediate section of the receiver coil has a transverse cross-sectional area that is substantially smaller than the transverse cross-sectional area of either of the first and second pole faces of the receiver coil.

14. The system of claim 10, wherein the receiver coil has a length substantially shorter than that of the transmitter coil, said shorter length causing a distance between centers of the first and second pole faces of said receiver coil to be less than a distance between centers of the first and second pole faces of said transmitter coil.

15. The system of claim 10, wherein a space separating the first and second pole faces of the transmitter coil is substantially greater than a thickness of a cutaneous layer of the patient's body that is disposed between the transmitter coil and the receiver coil.

16. The system of claim 10, wherein the intermediate section of the transmitter core comprises a first section and a second section that respectively terminate in the first pole face and the second pole face of the transmitter core, said first section having a first winding comprising a portion of the plurality of the turns of the electrical conductor, and said second section having a second winding comprising another portion of the plurality of the turns of the electrical conductor that is wound around the intermediate section of the transmitter core.

17. The system of claim 16, wherein the first section is directly coupled to the second section, and the transmitter core has a general V-shape.

18. The system of claim 10, wherein the intermediate sections of at least one of the transmitter coil and the receiver coil includes a mid-portion that is elongate and flattened, and which extends in a direction that is generally parallel to the first and second pole faces of said at least one of the transmitter coil and the receiver coil, said plurality of turns of the electrical conductor for said at least one of the transmitter coil and the receiver coil being wound around said mid-portion thereof.

19. The system of claim 10, wherein at least one of the transmitter core and the receiver core comprises a plurality of discrete elements formed of the magnetically permeable material that are separated by a dielectric material, to minimize losses in said at least one of the transmitter core and the receiver core, due to eddy currents.

20. A system for transferring power transcutaneously to energize an implanted medical device within a patient's body, comprising:
(a) a transmitter coil adapted to be disposed external to the patient's body, said transmitter coil including:
(i) a transmitter core of a magnetically permeable material having a first pole face coupled to a second pole face by an intermediate section, said transmitter core increasing in transverse cross-sectional size so that said first and second pole faces have an increased pole face area for conveying a transcutaneous magnetic flux; and
(ii) a plurality of turns of an electrical conductor wound around said intermediate section;
(b) a receiver coil adapted to be disposed subdermally, inside the patient's body, said receiver coil including:
(i) a receiver core of a substantially solid and magnetically permeable material having a first pole face coupled to a second pole face by an intermediate section, said receiver core increasing in transverse cross-sectional size so that said first and second pole faces of the receiver core have an increased pole face area for receiving a transcutaneous magnetic flux generated by the transmitter coil; and
(ii) a plurality of turns of an electrical conductor wound around said intermediate section and having ends adapted to couple to the medical device; and
(c) a power supply adapted to couple to the turns of the electrical conductor wound around the intermediate section of the transmitter core, said power supply supplying a time varying electrical current to energize the transmitter coil, producing an electromagnetic field that couples transcutaneously with the receiver coil, causing a corresponding electrical current to flow in the receiver coil for energizing the medical device implanted inside the patient's body.

21. The system of claim 20, wherein the intermediate section of the transmitter core comprises a first section and a second section that respectively terminate in the first pole face and the second pole face of the transmitter core, said first section having a first winding comprising a portion of the plurality of the turns of the electrical conductor, and said second section having a second winding comprising another portion of the plurality of the turns of the electrical conductor that is wound around the intermediate section of the transmitter core.

22. The system of claim 21, wherein the first section is directly coupled to the second section, and the transmitter core is a general V-shape.

23. The system of claim 21, wherein the intermediate section of the transmitter core further comprises a third section that extends between the first section and the second section, so that the transmitter core is generally U-shaped.

24. The system of claim 21, wherein the first and second sections of the transmitter core include angled portions disposed adjacent to the first and second pole faces of the transmitter core that turn the transmitter core to one side of the first and second pole faces, said first and second sections thereby extending generally to said one side of the first and second pole faces, so that said transmitter core has a low profile relative to the first and second pole faces of the transmitter core.

25. The system of claim 20, wherein the intermediate sections of at least one of the transmitter coil and the receiver coil includes a mid-portion that is elongate and flattened, and which extends in a direction that is generally parallel to the first and second pole faces of said at least one of the transmitter coil and the receiver coil, said plurality of turns of the electrical conductor for said at least one of the transmitter coil and the receiver coil being wound around said mid-portion thereof.

26. The system of claim 20, wherein at least one of the transmitter core and receiver core comprises a plurality of layers of the magnetically permeable material, adjacent layers of the magnetically permeable material being separated by a layer of a dielectric material, to minimize losses in said at least one of the transmitter core and receiver core due to eddy currents.

27. The system of claim 20, wherein at least one of the transmitter core and the receiver core comprises a plurality of discrete elements formed of the magnetically permeable material that are bonded together with a dielectric material, to minimize losses in said at least one of the transmitter core and the receiver core, due to eddy currents.

28. The system of claim 27, wherein the discrete elements comprise elongate rods that extend through said at least one of the transmitter core and the receiver core.

29. The system of claim 20, wherein the power supply provides a periodically varying electrical current to energize the transmitter coil.

30. The system of claim 29, wherein the periodically varying electrical current has a frequency less than 500 Hz.

31. The system of claim 20, wherein the receiver coil has a length that is substantially shorter than another length of the transmitter coil, the shorter length of said receiver coil causing a distance between centers of the first and second pole faces of said receiver coil to be less than a distance between centers of the first and second pole faces of said transmitter coil.

32. An electromagnetic coil configuration for conveying power transcutaneously, comprising:
   (a) a core of a magnetically permeable material, said core being V-shaped and having a first pole face coupled to a second pole face by an intermediate section, a transverse cross-sectional area of said intermediate section being substantially less than a transverse cross-sectional area of said first and second pole faces to provide an increased pole face area for conveying a transcutaneous magnetic flux; and
   (b) a plurality of turns of an electrical conductor wound around said intermediate section, said electrical conductor carrying an induced current if the coil is used as a receiver that is electromagnetically excited by an external source of the transcutaneous magnetic flux, and carrying a varying electrical current supplied by a power supply to which the electrical conductor is adapted to be connected if the coil is used as a transmitter of the transcutaneous magnetic flux.

33. A system for transferring power transcutaneously to energize an implanted medical device within a patient's body, comprising:
   (a) a transmitter coil adapted to be disposed external to the patient's body, said transmitter coil including:
      (i) a transmitter core of a magnetically permeable material, said transmitter core being V-shaped and having a first pole face coupled to a second pole face by an intermediate section; and
      (ii) a plurality of turns of an electrical conductor wound around said intermediate section;
   (b) a receiver coil adapted to be disposed subdermally, inside the patient's body, said receiver coil including:
      (i) a receiver core of a magnetically permeable material having a first pole face coupled to a second pole face by an intermediate section, said first and second pole faces having a substantially different transverse cross-sectional area than the first and second pole faces of the transmitter coil; and
      (ii) a plurality of turns of an electrical conductor wound around said intermediate section and having ends adapted to couple to the medical device; and
   (c) a power supply adapted to couple to the turns of the electrical conductor wound around the intermediate section of the transmitter core, said power supply supplying a time varying electrical current to energize the transmitter coil, producing an electromagnetic field that couples transcutaneously with the receiver coil, causing a corresponding electrical current to flow in the receiver coil for energizing the medical device implanted inside the patient's body.

34. A system for transferring power transcutaneously to energize an implanted medical device within a patient's body, comprising:
   (a) a transmitter coil adapted to be disposed external to the patient's body, said transmitter coil including:
      (i) a transmitter core of a magnetically permeable material, said transmitter core being V-shaped and having a first pole face coupled to a second pole face by an intermediate section, said transmitter core increasing in transverse cross-sectional size so that said first and second pole faces have an increased pole face area for conveying a transcutaneous magnetic flux; and
      (ii) a plurality of turns of an electrical conductor wound around said intermediate section;
   (b) a receiver coil and adapted to be disposed subdermally, inside the patient's body, said receiver coil including:
      (i) a receiver core of a magnetically permeable material having a first pole face coupled to a second pole face by an intermediate section, said receiver core increasing in transverse cross-sectional size so that said first and second pole faces of the receiver core have an increased pole face area for receiving a transcutaneous magnetic flux generated by the transmitter coil; and
      (ii) a plurality of turns of an electrical conductor wound around said intermediate section and having ends adapted to couple to the medical device; and
   (c) a power supply adapted to couple to the turns of the electrical conductor wound around the intermediate section of the transmitter core, said power supply supplying a time varying electrical current to energize the transmitter coil, producing an electromagnetic field that couples transcutaneously with the receiver coil, causing a corresponding electrical current to flow in the receiver coil for energizing the medical device implanted inside the patient's body.

* * * * *

UNITED STATES PATENT AND TRADEMARK OFFICE
CERTIFICATE OF CORRECTION

PATENT NO. : 5,741,316
DATED : April 21, 1998
INVENTOR(S) : James C. Chen et al.

It is certified that error appears in the above-indentified patent and that said Letters Patent is hereby corrected as shown below:

On title page,

| | |
|---|---|
| Section [56], References Cited, Other Publications, 3rd Reference | "Automated" should read --Autotuned-- |
| Section [56], References Cited, Other Publications, 10th Reference | "#PH-43067-1414" should read --#PH-43-67-1414-- |
| Column 8, line 44 (Claim 10, line 6) | "corn" should read --core-- |
| Column 10, line 36 (Claim 22, line 3) | "is" should read --has-- |

Signed and Sealed this

Twenty-ninth Day of December, 1998

Attest:

BRUCE LEHMAN

*Attesting Officer*  *Commissioner of Patents and Trademarks*